United States Patent [19]

Erickson

[11] Patent Number: 5,494,158

[45] Date of Patent: Feb. 27, 1996

[54] SYRINGE SALES AND DISPOSAL BOX

[75] Inventor: Charles W. Erickson, Minneapolis, Minn.

[73] Assignee: MMCT Holdings, LLC, St. Paul, Minn.

[21] Appl. No.: 366,124

[22] Filed: Dec. 29, 1994

[51] Int. Cl.⁶ .................................................. B65D 43/14
[52] U.S. Cl. ......................... 206/366; 206/1.5; 206/370; 220/908
[58] Field of Search .......................... 206/1.5, 366, 370, 206/438, 443; 220/908

[56] References Cited

U.S. PATENT DOCUMENTS

| | | | |
|---|---|---|---|
| 4,453,648 | 6/1984 | Harris et al. | 206/370 |
| 4,580,688 | 4/1986 | Harris et al. | 206/366 |
| 4,779,728 | 10/1988 | Hanifl et al. | 206/366 |
| 4,842,138 | 6/1989 | Sandel et al. | 206/366 |
| 4,874,103 | 10/1989 | Quisenberry et al. | 220/908 |
| 4,877,150 | 10/1989 | Otto et al. | 206/366 |
| 4,890,733 | 1/1990 | Anderson | 206/366 |
| 4,903,832 | 2/1990 | Stewart | 206/366 |
| 5,107,990 | 4/1992 | Wicherski et al. | 206/366 |
| 5,184,720 | 2/1993 | Packer et al. | 206/366 |

Primary Examiner—Jimmy G. Foster
Attorney, Agent, or Firm—Roger W. Jensen

[57] ABSTRACT

A box for shipping unused syringes after syringe manufacture to the point of syringe usage (whereat all unused syringes are removed from said box), said box then being usable for the safe storage of used syringes. The box has an open-topped container having a bottom and a plurality of sides, a cover for closing off said container during said shipment and being selectably movable with respect to said container so as to permit the bulk removal of all unused syringes, therein, means for reclosing said container including said cover and means locking said cover means to said container. The box also has means for the serial feeding of used syringes into said closed and locked container including used syringe receiving means integral with said box and having a first operative position for receiving a used syringe external of said box and being movable to a second operative position whereat said used syringe is discharged for safe storage thereof into said box following which said syringe receiving means may be returned to said first operating position for the serial receiving of additional used syringes for safe storage thereof in said box, said syringe receiving means being further characterized by including means for preventing used syringes internal of said locked box from being removed from said box via said syringe receiving means.

16 Claims, 6 Drawing Sheets

SYRINGE SALES AND DISPOSAL BOX

BACKGROUND OF THE INVENTION

A world-wide health care problem and need is the disposal of used syringes; this is a continuing health threat to the public. Of great concern, of course, are AIDS and other serious infectious diseases such as hepatitis.

Health care regulations have mandated the safe disposal of used syringes. A number of approaches, procedures and apparatus have been proposed for the storage of used syringes and the subsequent disposal thereof.

After a needle has been used either by or on a patient, then the syringe needle is contaminated from contact with the blood of the patient. If the user is HIV positive or a carrier of hepatitis or other blood born pathogen, then an accidental needle stick by the contaminated needle could spread the disease.

In hospitals and clinics the health care industry uses special containers dedicated for the disposal of needles and other invasive devices. Such containers are frequently referred to as "sharps" containers. The sharps containers with used syringes/needles therein are then disposed by industrial waste collectors and are usually either burned, disintegrated or buried, depending upon local health care regulations.

There is an additional dimension to the problem; that is the uses of syringes in private homes. For example, home syringe users are frequently diabetics who require frequent doses of insulin to regulate their glucose level. The practice of disposing and safe storage of used syringe syringes in private homes is far less organized than in hospitals and clinics. Home disposing techniques are varied and frequently home invented, using discarded or empty containers found around the home; such arrangements are high risk for accidental spreading of disease. There is currently no standard disposal practice for insulin users.

SUMMARY AND OBJECTS OF THE INVENTION

Simply stated, the predominant object of the present invention is to provide an improved syringe sales and disposal box with the present invention being especially appropriate for solving the problem in private homes. The present invention provides for safe disposal of used syringes by incorporating the disposal box into the initial sales box. Syringes would be sold at the pharmacy or distribution point in an industry standard box of, for example, 100 syringes packaged 10 to a plastic bag. The diabetic patient would purchase the entire box of 100 syringes at the pharmacy or distribution point and, upon taking the box home, the diabetic patient or other support person would remove all ten bags from the sales/disposal box by opening the cover that had been sealed at the factory which manufactured the syringes. Once the box was emptied, then the cover would be resealed and locked to the box, i.e., the cover would be permanently closed.

Then the individual used syringes would, immediately after use, be loaded into the box by usage of a unique feeding mechanism that would permit used syringes to be placed for safe storage in the box. The feeding mechanism is further characterized by permitting individual used syringes to be inserted into the box but to prevent any syringe within the box from being removed from the box. The box with used syringes therein then can be safely transported or disposed of according to local ordnances and health regulations or could be returned to a central collection point for destruction. The box is intended to be nonreusable and would be destroyed along with the used syringes contained therein.

In brief summary, the disposal box provided by this invention comprises an open topped container having a bottom and a plurality of sides integral with the bottom. The bottom and sides define a preselected volume for the storing, during shipment, of a preselected quantity of unused syringes. The box further includes a cover means for closing off the container during shipment. The cover is selectively movable with respect to the container so as to permit the bulk removal by the consumer of all of the preselected quantity of unused syringes. The invention further provides means for reclosing the container which includes the cover means and additional nonreversible locking means locking the cover means to the container.

The invention further includes means for the serial feeding of used syringes into the closed and locked container including used syringe receiving means integral with the exterior of the box, the used syringe receiving means having a first operative position for receiving a used syringe external of said box and being movable to a second operative position whereat said used syringe is discharged for safe storage thereof into said box following which said syringe receiving means may be returned to said first operating position for the serial receiving of additional new syringes for safe storage in the box. The syringe receiving means is further characterized by including means for preventing used syringes internal of said box from being removed from said box via said syringe receiving means.

DETAILED DESCRIPTION OF THE INVENTION

Figures 1, 1A, 1B, 2:
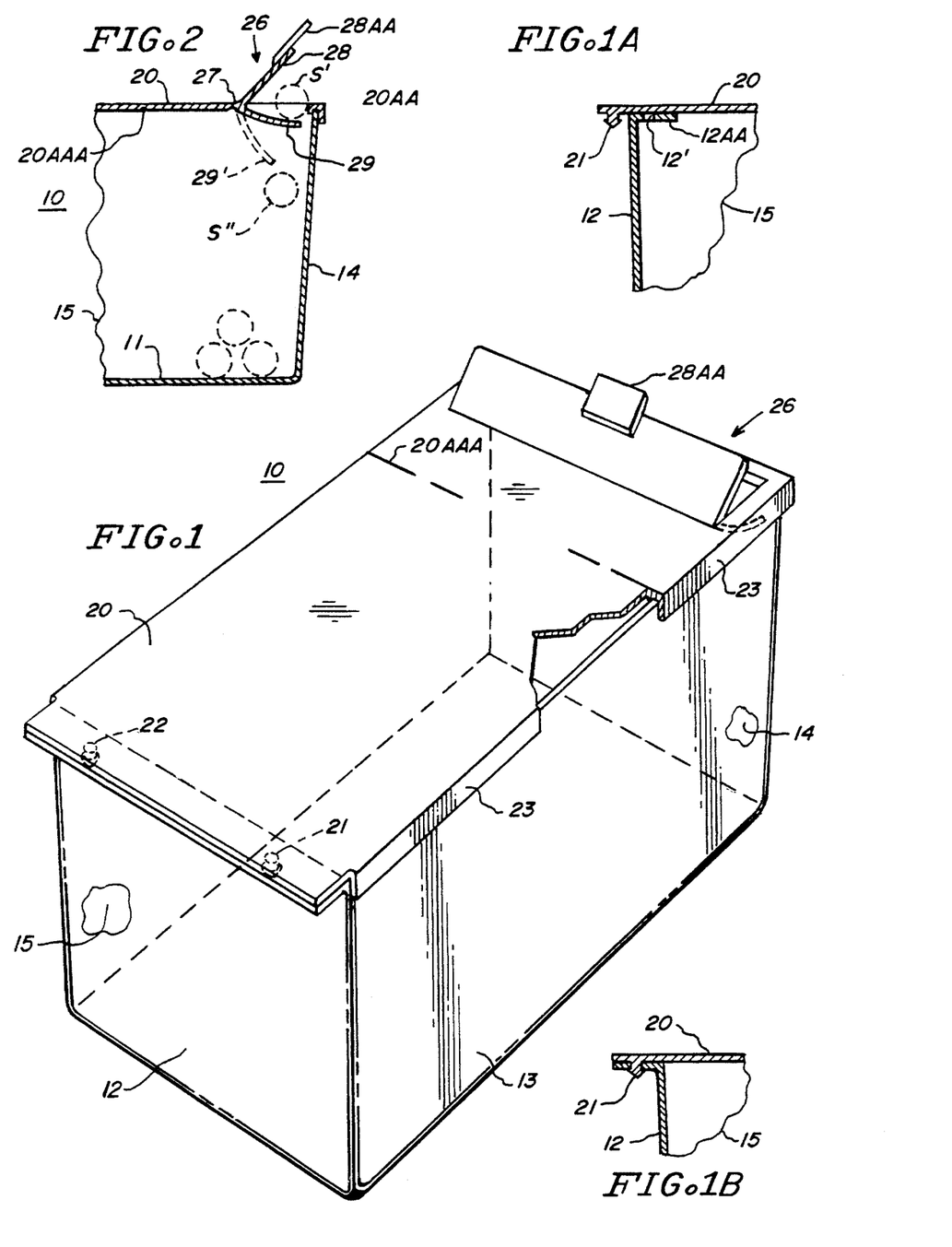
FIG. 1 is an isometric depiction of a first embodiment of the invention.
FIG. 1A shows a detail of the cover and the box during initial shipment from the syringe factory to the consumer and FIG. 1B shows a corresponding detail of the box of FIG. 1 after the consumer has removed the unused syringes and the cover has been permanently locked to the container.
FIG. 2 shows a partial cross section of the box shown in FIG. 1 and shows the used syringe receiving means.

Referring to FIG. 1, the reference numeral 10 generally designates a box for shipping unused syringes after syringe manufacture to the point of syringe usage. The box 10 comprises an open top container having a bottom 11 and a plurality of sides 12, 13, 14 and 15 integral therewith with the bottom and sides defining a preselected volume for storing, for shipment, of a preselected quantity of unused syringes, not shown.

The box further includes a cover means 20 for closing off the container during said shipment and being selectively movable with respect to the container so as to permit the bulk removal of all of the preselected quantity of unused syringes. More specifically, the cover 20 has preselected dimensions so that it completely covers the opened top of the container as depicted in FIG. 1. As shown in FIG. 2, a first end of the cover 20 is connected to the top of side 14 with a pivotable means 20AA, the function of which is to permit the entire cover to be temporarily raised away from the container so as to permit the initial packing and storage of unused syringes at the syringe factory and then the unpacking and removal of the unused syringes by the consumer. An alternative to pivot means 20AA would be an intermediate pivot 20AAA in cover 20 positioned as shown in FIGS. 1 and 2. The other end of the cover 20 has a preselected length so that it extends slightly beyond the side 12 as is clearly depicted in FIGS. 1A and 1B. During the initial shipment of syringes from the factory, the top 12AA of side 12 is folded inwardly of the box as is shown in FIG. 1A. At that time the underside of the cover 20 is abutting the upper surface of portion 12AA. After the unused syringes are removed from the box, then the portion 12AA of side 12 is flipped 180 degrees or rotated to the position shown in FIG. 1B in which position one or more locking tabs 21 and 22 are pushed through preselected holes or openings 12' in portion 12AA of side 12. The locking action is unidirectional, i.e., the tabs 21 can be forced into and through the openings 12' but cannot be thereafter removed.

If desired the cover 20 may have one or more side flanges 23 along the edges thereof.

The used syringe receiving means for this embodiment of the invention is designated by reference numeral 26 and comprises a movable flap pivotally attached as at 27 to the cover 20 near one end thereof as shown in FIG. 2. As shown in FIG. 1, the flap 26 extends transversely across the cover 20. The pivotal connection 27 may be provided by having the cover 20 made of plastic and the plastic being scored at 27 to permit flexing and also to normally hold the flap 26 in the solid line position shown in FIG. 2. The flap has two main surfaces or portions 28 and 29 which are joined at 27 but then diverge to form a "V" shaped cross-section as shown clearly in FIG. 2. In the normal position the portion 29 closes off the box and also may receive a used syringe S' as shown in FIG. 2, following which force may be applied to a tab 28AA integral with portion 28 and the flap 26 then is displaced and rotated (clockwise as shown in FIG. 2) about pivot point 27 so that portion 29 is positioned to that shown by dotted lines 29' in FIG. 2 at which position the used syringe is dropped down into the box, the used syringe at this point of the safe disposal procedure being designated by the reference symbol S". Additional used syringes are shown in the bottom of the box.

It will be understood that used syringes in the box can not be removed via the flap 26; portion 29 blocks such removal. Thus the used syringe receiving means is unidirectional in that it permits syringes to be inserted into the box but, as noted, once a syringe is in the box, then it can not be removed via flap 29.

Figure 3:
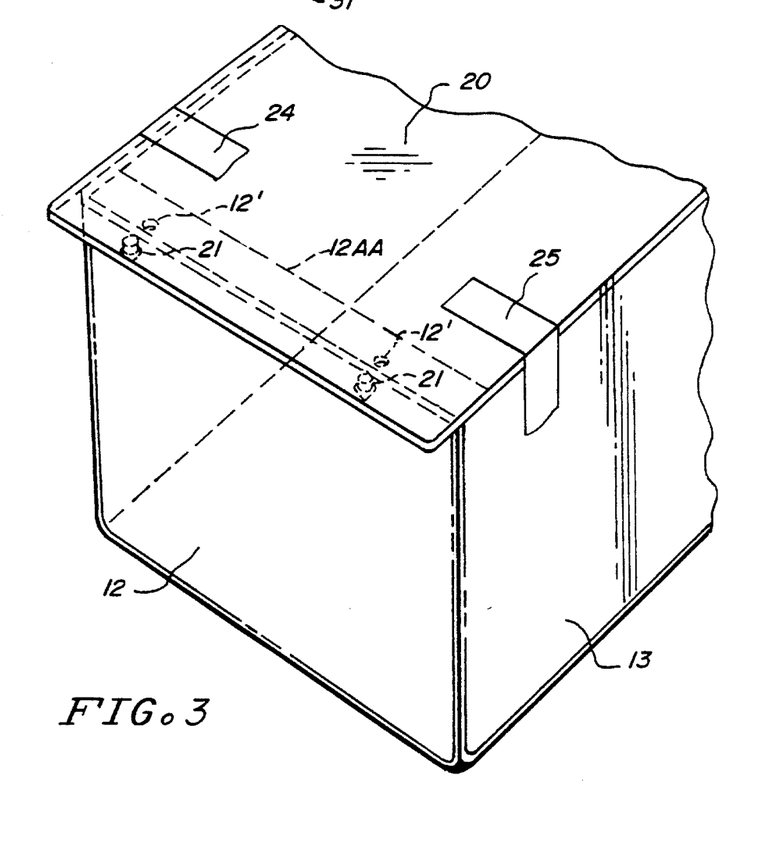
FIG. 3 shows another partial view of the box of FIG. 1 while the box is in shipment and prior to the time of being opened by the ultimate consumer.

Referring again to FIG. 1A when the box is being used for shipment to the consumer, then the cover 20 is held fixed to the container by suitable means such as tape 24 and 25 shown in FIG. 3.

Figures 4, 4A:
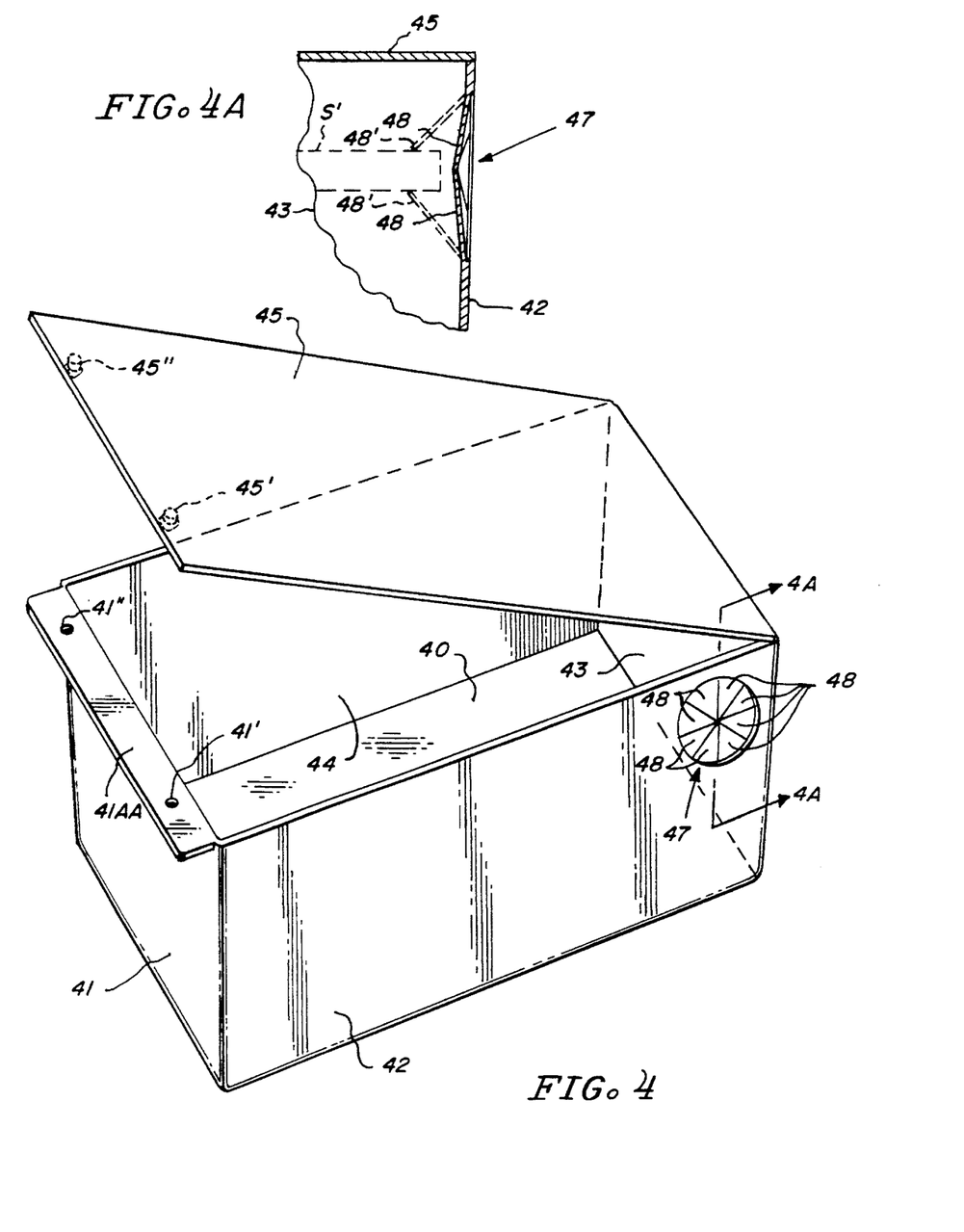
FIG. 4 shows another embodiment of the invention and FIG. 4A is a view of the used syringe receiving means of the box of FIG. 4 as viewed along the section lines 4A—4A.

The preferred embodiment of the invention is shown in FIGS. 4 and 4A wherein a box is shown having numerous similarities to the box of the embodiment shown in FIG. 1. A key difference between this embodiment is that the used syringe receiving means is integral with one of the sides of the box as shown in FIG. 4, although it should be understood that the used syringe receiving means could be integral with the top of the box shown in FIG. 4. Thus the box of FIG. 4 comprises a bottom 40, four sides 41, 42, 43 and 44 and a top 45. Positioned in the side 42 is a used syringe receiving means or structure 47 comprising a plurality of tabs 48 arranged in a generally circular configuration with each tab 48 extending from the side 42 and extending radially toward the center of said circular configuration. The tabs 48 may be made of plastic and may in fact be integral with the side 42, i.e., made of the same plastic as the box. As seen in FIG. 4 each tab 48 has a shape of a piece of pie so that they collectively comprise a complete pie or circle. The tabs 48 have a normally closed position as shown in FIGS. 4 and 4A and, in said closed position, the tabs would collectively close off the box. On the other hand, the resiliency or flexing of the tabs permits the inner tips at the center of the configuration to be displaced inwardly of the box on a temporary basis indicated by the dotted lines 48' under the force of a used syringe S' being inserted for safe storage thereof into the box following which the biasing means functions to close off the box as aforesaid.

In FIG. 4 it will be noted that the top of side 41 has a portion 41AA which corresponds to portion 12AA of the embodiment of FIGS. 1, 1A and 1B. Further portion 41AA has a pair of apertures therethrough 41' and 41" adapted to coact with locking pins 45' and 45" at the end of cover 45.

Figure 5:
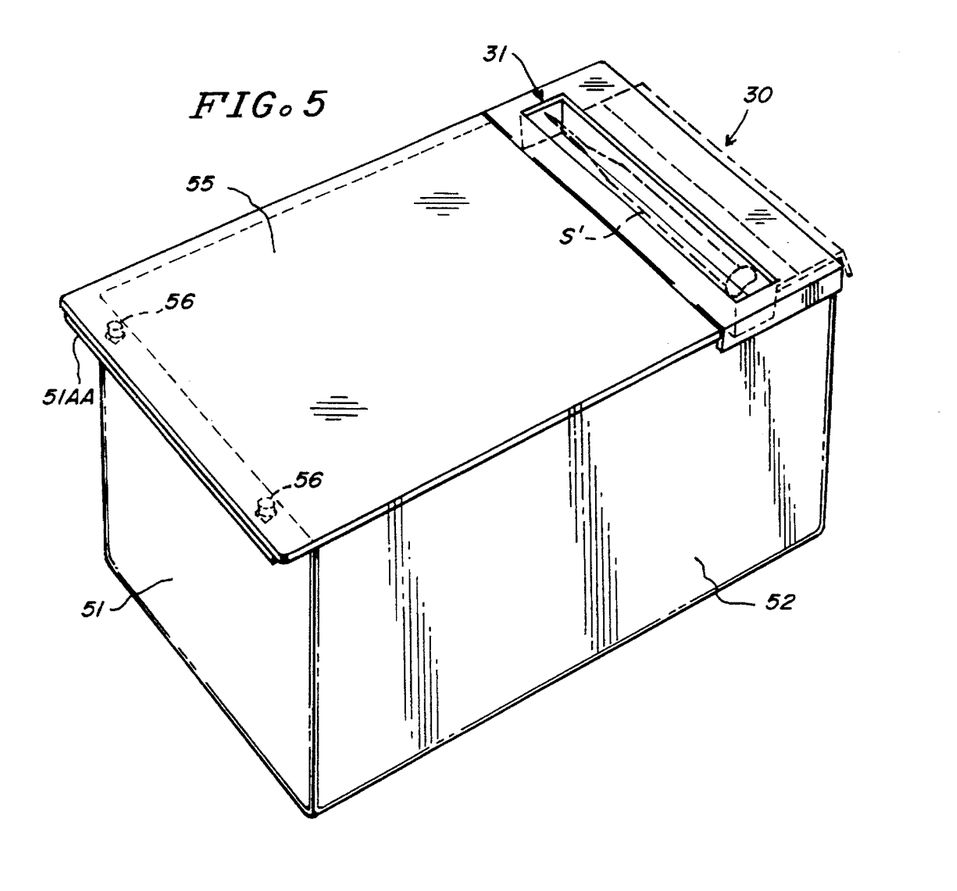
FIG. 5 shows another embodiment of the invention.
Figure 5A:
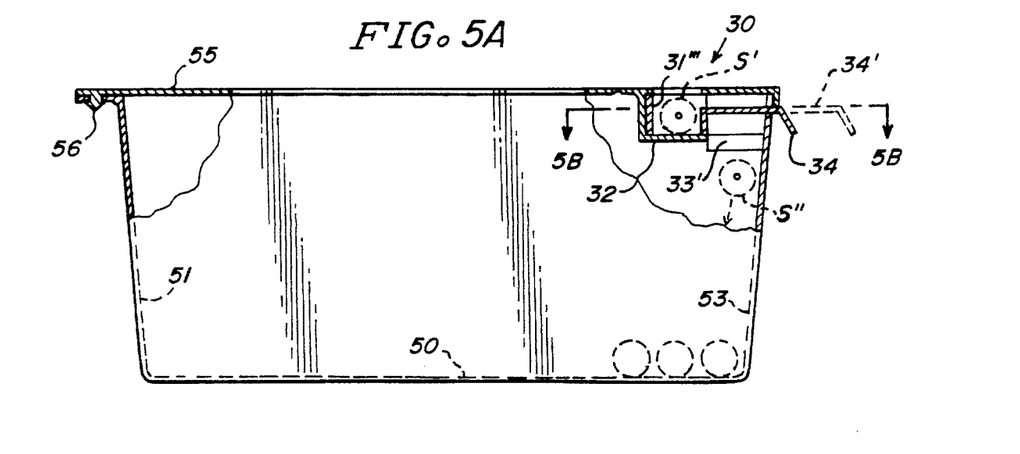
FIGS. 5A and 5B are cross sections as viewed along section lines 5A—5A and 5B—5B respectively of FIG. 5.
Figure 5B:
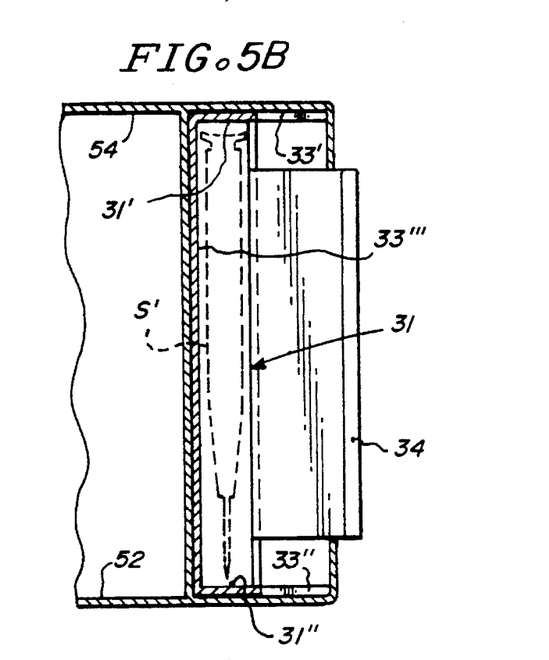

Another embodiment of the invention is depicted in FIGS. 5, 5A and 5B wherein the used syringe receiving means is integral with the top of the box, the box being defined in this embodiment by an open topped container having a bottom 50 and four sides 51, 52, 53 and 54 integral therewith as well as a cover means 55 for closing off the top of the container. Again, there are strong similarities between the basic boxes depicted in the first two above described embodiments and the box shown in FIGS. 5 and 5A. For example, the cover 55 in FIG. 5 may have one or more locking tabs 56 coacting with mating apertures in a foldable top portion 51AA of side 51.

Further the box would be used to ship new, i.e., unused syringes from the factory to the consumer; at this time the portion 51AA would be folded in (similar to FIG. 1A) and the top 55 would be secured in place by suitable means such as tape similar to 24 and 25 of FIG. 3.

After the new/unused syringes were removed and the cover locked, then used syringes may be safely disposed and stored by the used syringe receiving means identified by reference number 30 and which comprises a four sided elongated box 31 having an open top and an open bottom having a preselected length and width for receiving a used syringe. The box 31 is supported for limited horizontal movement on a bracket 32 which is connected to the underside of the cover 55. Further the box 31 has short side members 31' and 31" which are adapted to coact with a pair of shoulders 33' and 33" respectively which are aligned with the bottom of bracket 32. A latch 34 is connected to box 31 and is shown in the used syringe receiving position in FIG. 5A, a used syringe S' being depicted in the box 31. The consumer then would pull the latch 34 outwardly to the position designated by the reference 34'. The box 31 also is moved outwardly with the latch and the used syringe is carried along by a long side 31''' of box 31 to the point where it is clear of supporting bracket 32 at which point it falls as S'' through the open bottom of box 31 down into the box for safe storage. The storage function is unidirectional. Used syringes in the box may not be removed via means 30 because the latch 34 is returned to the position shown in FIG. 5A either manually or by spring means, not shown.

Figures 6, 6A:
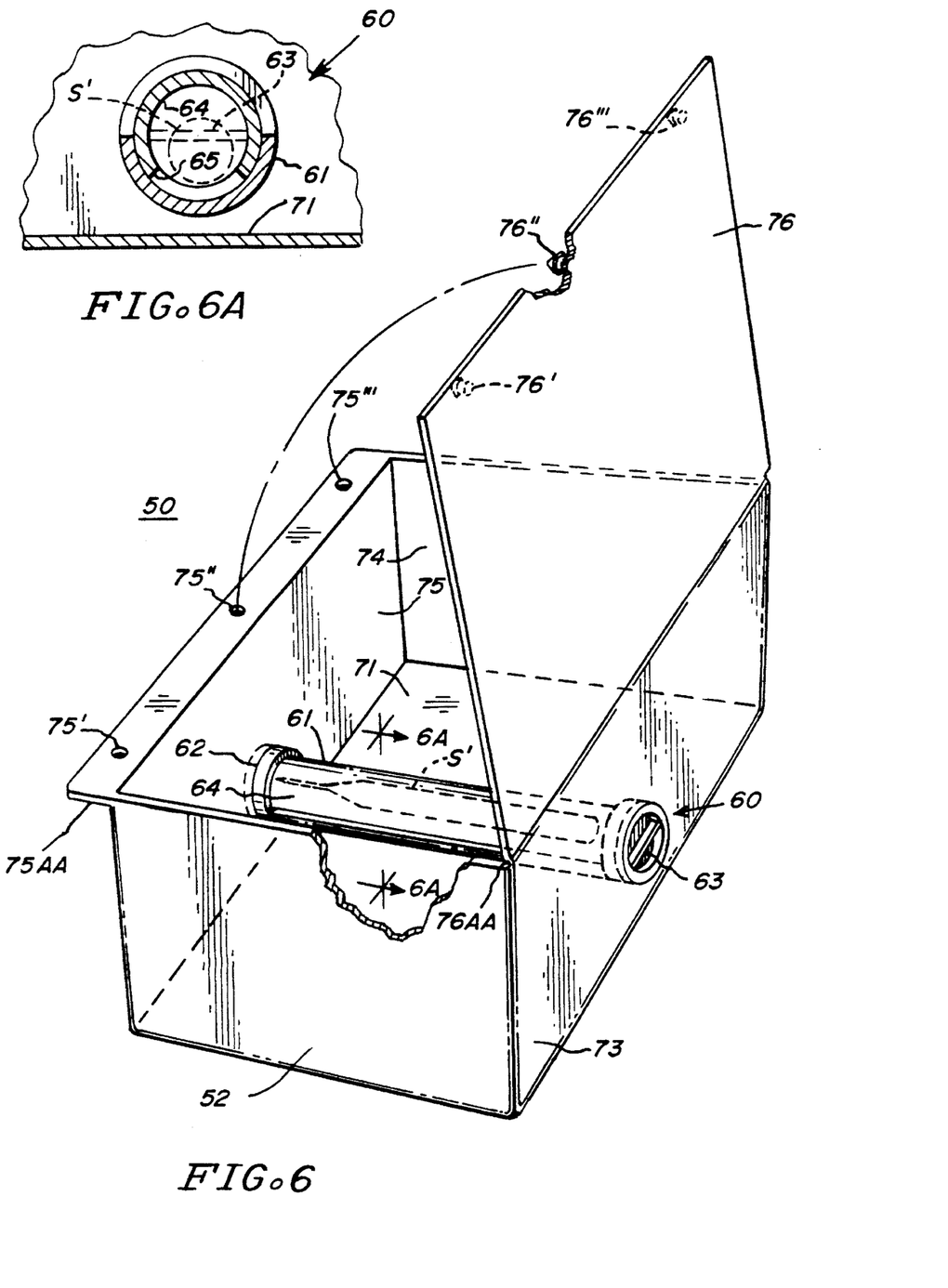
FIG. 6 shows yet another embodiment of the invention and FIG. 6A is a view of the used syringe receiving means of the box of FIG. 6 as viewed along the section lines 6A—6A.

Another embodiment of the invention is shown in FIGS. 6 and 6A wherein a box 70 is provided which is generally similar to the previously described boxes where the basic container is comprised of a bottom 71 and four sides 72, 73, 74 and 75. Box side 75 has a top flap 75AA which corresponds in function with portion 12AA shown in FIG. 1A. A cover 76 is hinged at 76AA to the top of side 73 and has a plurality of locking tabs 76', 76'' and 76''' adapted to coact with suitable apertures 75', 75'' and 75''' respectively of top flap 75AA to lock the cover to the box when so desired.

In FIG. 6 the used syringe receiving means comprising a tubular means 60 rotatably supported by sides 73 and 75. The tubular means 60 includes a support or drum 61 fixed to the sides 73 and 75 and has a cup-shaped cross section. The rotary drum 64 having a longitudinal opening 65 and a cup-shaped cross-section, and is positioned for rotation within drum 61 and is rotatable about its longitudinal axis manually through operation of a torque means 63.

After the cover is locked to the box, then the box 70 is turned 180 degrees or upside down so that the cover 76 becomes temporarily the bottom of the box. In this position the tubular means 60 is in the top most position of the box. Then used syringes may be serially and safely stored in the box as follows. The torque means 63 rotates the cup-like rotary drum 64 so that the opening 65 is facing upwardly. Then a used syringe S' may be inserted through an opening 62 in side 75 which is in register with drum 61. When a used syringe is lying in the rotary cup-shaped drum 64 as depicted in FIG. 6, and then the drum 64 is rotated a half turn and the used syringe will then drop into the locked container.

Figure 7:
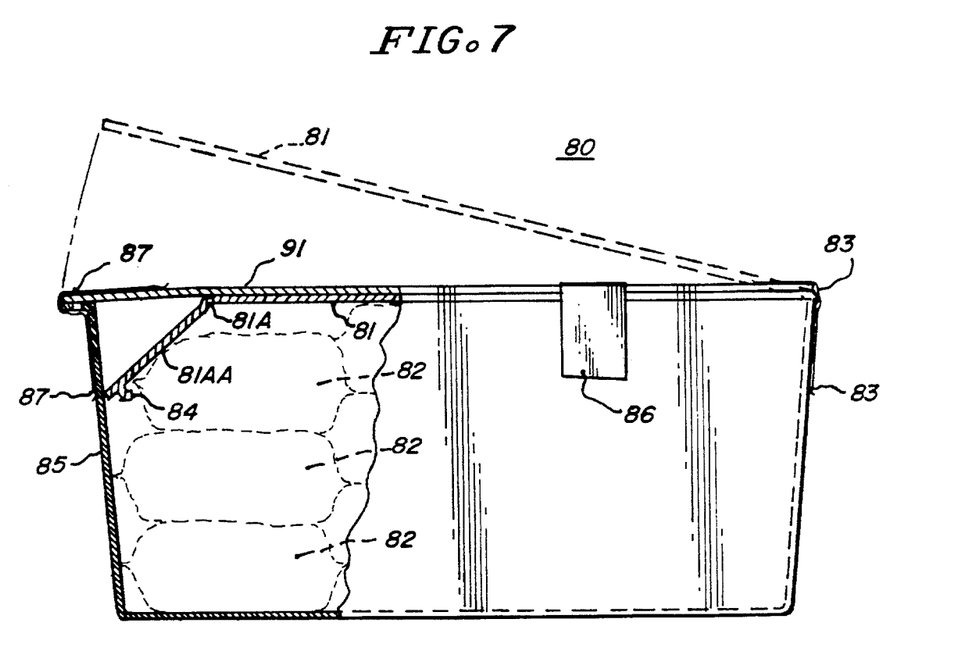
FIG. 7 is another embodiment of the invention showing a box in accordance to any of the preceding embodiments further characterized by including an auxiliary cover means overlying the first cover means.
Figure 7A:
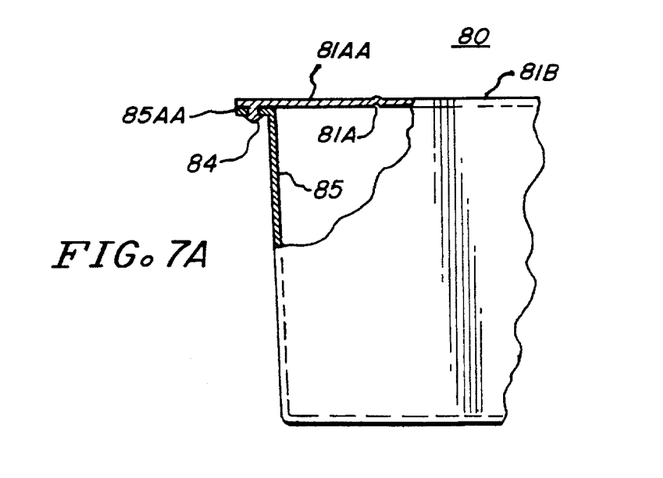
FIG. 7A shows a detail of the box after the disposal cover has been locked.

FIGS. 7 and 7A show a further modification of the invention in that a box 80 is provided with a first cover means 81 and an auxiliary cover means 91. The first cover means 81 is the disposal cover and is intended to be permanently attached to the box as, for example, by a pivot means 83 so that the cover may be opened at the new syringe factory or shipping facility so as to receive a plurality of new/unused syringes shown in FIG. 7 as a number of bags 82 each containing a preselected number, e.g., 10 of individually packaged syringes.

The cover 81 has a portion 81AA which is at the opposite end from pivot 83. Portion 81AA is pivoted at 81A so the cover 81 may be completely stored in the box during shipment.

The cover 81 may have on the upper surface 81B an appropriate warning label (not shown) as may be desired or required by applicable governmental regulations.

The disposal cover 81 and/or box 80 may also include used syringe receiving means (not shown) of the types shown in the previously described embodiments for the safe storage of used syringes.

The auxiliary cover means 91 has a primary function of being a temporary extra cover which overlays the permanent disposal cover 81 from the new syringe factory to the consumer who then removes and discards cover 91. Cover 91 may have thereon sales or product identification information (not shown) to facilitate the distribution of the enclosed syringes to the ultimate consumer. Once the consumer discards the cover 91 then the consumer sees the top 81B of cover 81 which, in addition to the optional hazardous waste warning, may have instructions to the consumer for use of the apparatus. For example, the consumer would be instructed (i) to remove the bags 82 for future use of the enclosed new/unused syringes, and (ii) to lock cover 81 to the box by use of appropriate locking means, e.g., locking tabs 84 which are integral with end portion 81AA and which coact with suitable apertures in a flange 85AA on the top of a side or end section of box 80.

To secure the auxiliary cover 91 to the disposal cover 81 during shipment to the consumer, suitable fastening means such as tape pieces 86 and 87 may be utilized.

While I have described a preferred embodiment of the invention, it will be understood that the invention is limited only by the scope of the following claims.

The embodiments of the invention in which an exclusive property right is claimed are defined as follows:

1. A box for transporting unused syringes after syringe manufacture to the point of syringe usage (whereat all unused syringes are removed from said box), said box then being usable for the safe storage of used syringes, said box comprising:
   a) an open-topped container having a bottom and a plurality of sides integral therewith with said bottom and sides defining a preselected volume for storing of a preselected quantity of unused syringes,
   b) a cover means for closing off said container during said storage and being selectably movable with respect to said container so as to permit the bulk removal of all of said preselected quantity of unused syringes,
   c) means for reclosing said container including said cover means and additional nonreversible locking means locking said cover means to said container, and
   d) means for the serial feeding of used syringes into said closed and locked container including used syringe receiving means integral with said box and having a first operative position for receiving a used syringe external of said box and being movable to a second operative position whereat said used syringe is discharged for safe storage thereof into said box following which said syringe receiving means may be returned to said first operating position for the serial receiving of additional used syringes for safe storage thereof in said box, said syringe receiving means being further characterized by including means for preventing used syringes internal of said box from being removed from said box via said syringe receiving means.

2. Apparatus of claim 1 further characterized by said syringe receiving means including a structure integral with said cover means.

3. Apparatus of claim 1 wherein said cover means is pivotally connected at one end thereof to one of said sides and said syringe receiving means includes a structure integral with said cover means and located adjacent to said one end.

4. Apparatus of claim 3 wherein said structure is further characterized by having a syringe receiving surface having a first position for receiving a used syringe and being manually displaceable to a second position within said box whereat a used syringe resting thereon is discharged into said box.

5. Apparatus of claim 4 wherein said structure further includes means for resiliently connecting said surface to said cover means so as to return said surface to said first position upon the withdrawal of manual force from said surface.

6. Apparatus of claim 5 wherein said surface is pivotally connected to said cover means and said surface is rotatable from said first position downwardly into said box to said second position.

7. Apparatus of claim 5 wherein said surface is manually displaced from said first position longitudinally to said second position.

8. Apparatus of claim 1 wherein said syringe receiving means comprises a tubular means rotatably supported by said sides for rotation about a longitudinal axis thereof and positioned within said box, said tubular means further having an opening adjacent to one of said sides for receiving a used syringe and syringe release means, and means for rotating said tubular means about said longitudinal axis whereby a used syringe is released from said tubular means by said release means and thereby discharged into said box.

9. Apparatus of claim 1 wherein said syringe receiving means includes a structure integral with one of said plurality of said sides.

10. Apparatus of either claim 2 or claim 9 wherein said structure is further characterized by having a plurality of tabs arranged in a generally closed configuration with each tab connected to and depending from the box and extending radially toward the center of said configuration, means for biasing said tabs to a normally closed position so that said tabs collectively close off said box and for permitting the central tips thereof to be displaced inwardly of said box on a temporary basis under the force of a used syringe being inserted for safe storage thereof into said box following which said biasing means functions to close off said box as aforesaid.

11. Apparatus of claim 1 further characterized by including: an auxiliary cover means overlying said first mentioned cover means.

12. Apparatus of claim 1 wherein said cover means is pivotally connected at one end thereof to one of said sides and said syringe receiving means includes a structure integral with said box.

13. Apparatus of claim 12 wherein said structure is further characterized by having a syringe receiving surface having a first position for receiving a used syringe and being manually displaceable to a second position within said box whereat a used syringe resting thereon is discharged for safe storage into said box.

14. Apparatus of claim 13 wherein said structure further includes means for resiliently connected said surface to said box so as to return said surface to said first position upon the withdrawal of manual force from said surface.

15. Apparatus of claim 14 wherein said surface is pivotally connected to said box and said surface is rotatable from said first position inwardly into said box to said second position.

16. Apparatus of claim 14 wherein said surface is manually displaced from said first position longitudinally to said second position,

* * * * *